US010406178B2

(12) United States Patent
Borrello et al.

(10) Patent No.: US 10,406,178 B2
(45) Date of Patent: *Sep. 10, 2019

(54) ACTIVATION OF MARROW INFILTRATING LYMPHOCYTES IN HYPOXIC ALTERNATING WITH NORMOXIC CONDITIONS

(71) Applicant: The Johns Hopkins University, Baltimore, MD (US)

(72) Inventors: Ivan M. Borrello, Baltimore, MD (US); Kimberly A. Noonan, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/606,766

(22) Filed: May 26, 2017

(65) Prior Publication Data

US 2017/0258838 A1 Sep. 14, 2017

Related U.S. Application Data

(63) Continuation of application No. 15/112,353, filed as application No. PCT/US2015/048536 on Sep. 4, 2015, now Pat. No. 9,687,510.

(60) Provisional application No. 62/186,040, filed on Jun. 29, 2015, provisional application No. 62/045,782, filed on Sep. 4, 2014.

(51) Int. Cl.
*A61K 35/17* (2015.01)
*C12N 5/0783* (2010.01)
*C12N 5/077* (2010.01)
*A61P 35/00* (2006.01)
*A61K 35/12* (2015.01)

(52) U.S. Cl.
CPC .............. *A61K 35/17* (2013.01); *A61P 35/00* (2018.01); *C12N 5/0636* (2013.01); *C12N 5/0669* (2013.01); *A61K 2035/124* (2013.01); *C12N 2500/02* (2013.01); *C12N 2501/2302* (2013.01); *C12N 2501/998* (2013.01)

(58) Field of Classification Search
None
See application file for complete search history.

(56) References Cited

U.S. PATENT DOCUMENTS

| | | |
|---|---|---|
| 2010/0178299 A1 | 7/2010 | Sitkovsky et al. |
| 2011/0223146 A1 | 9/2011 | Borrello et al. |
| 2014/0255947 A1 | 9/2014 | Irarrazabal |
| 2014/0377240 A1 | 12/2014 | Sitkovsky et al. |

FOREIGN PATENT DOCUMENTS

| | | |
|---|---|---|
| WO | WO-00/50571 A1 | 8/2000 |
| WO | WO-2013/109759 A1 | 7/2013 |
| WO | WO-2014/085437 A2 | 6/2014 |

OTHER PUBLICATIONS

Atkuri et al., "Importance of culturing primary lymphocytes at physiological oxygen levels," Proc Natl Acad Sci, 104(11):4547-52 (2007).
By et al., "Fall in Oxygen Tension of Culture Medium Stimulates the Adenosinergic Signalling of a Human T Cell Line," Purinerg Signal, 8:661-667 (2012).
Caldwell et al., "Differential effects of physiologically relevant hypoxic conditions on T lymphocyte development and effector functions," J Immunol, 167(11):6140-6149 (2001).
Clambey et al., "Hypoxia-inducible Factor-1 Alpha-dependent Induction of FoxP3 Drives Regulatory T-cell Abundance and Function During Inflammatory Hypoxia of the Mucosa," Proc Natl Acad Sci USA, 109(41): E2784-E2793 (2012).
Extended European Search Report issued by the European Patent Office in corresponding Application No. 15828258.8, dated Apr. 18, 2018.
Hardy et al., "Costimulated tumor-infiltrating lymphocytes are a feasible and safe alternative donor cell therapy for relapse after allogeneic stem cell transplantation," Blood, 119(12):2956-9 (2012).
Luznik et al., "High-dose, post-transplantation cyclophosphamide to promote graft-host tolerance after allogeneic hematopoietic stem cell transplantation," Immunol Res, 47(1-3):65-77 (2010).
Makino et al., "Hypoxia-inducible factor regulates survival of antigen receptor-driven T cells," J Immunol, 171:6534-40 (2003).
Noonan et al., "Activated marrow-infiltrating lymphocytes effectively target plasma cells and their clonogenic precursors," Cancer Res, 65(5):2026-34 (2005).
Noonan et al., "Adoptive Transfer of Activated Marrow-infiltrating Lymphocytes Induces Measurable Antitumor Immunity in the Bone Marrow in Multiple Myeloma," Sci Transl Med, 7(288): 288ra78, p. 1-14 (2015).
Noonan et al., "The immune microenvironment of myeloma," Cancer Microenvironment, 4:313-323 (2011).
Ohta et al., "Hypoxia-induced and A2A Adenosine Receptor-independent T-cell Suppression is Short Lived and Easily Reversible," Int Immunol, 26(2): 83-91 (2014).
Robbins et al., "Hypoxia modulates early events in T cell receptor□mediated activation in human T lymphocytes via Kv1. 3 channels," J Physiol, 564(1):131-143 (2005).
Roman et al., "T-cell activation under hypoxic conditions enhances IFN-y secretion," Am J Respir Cell Mol Biol, 42:123-8 (2010).
Semenza, "Oxygen Sensing, Hypoxia-Inducible Factors, and Disease Pathophysiology," Annu Rev Pathol Mech Dis, 9: 47-71 (2014).

(Continued)

*Primary Examiner* — Michail A Belyavskyi
(74) *Attorney, Agent, or Firm* — Foley Hoag LLP

(57) ABSTRACT

In some aspects, the invention relates to compositions comprising marrow infiltrating lymphocytes ("MILs"). The MILs may be activated MILs. In some aspects, the invention relates to methods for activating MILs, comprising incubating MILs in an environment comprising less than 21% oxygen. In some aspects, the invention relates to methods for treating cancer in a subject, comprising administering to the subject a composition comprising activated MILs.

20 Claims, 13 Drawing Sheets

(56) References Cited

OTHER PUBLICATIONS

Shi et al., "Combining Antiangiogenic Therapy with Adoptive Cell Immunotherapy Exerts Better Antitumor Effects in Non-Small Cell Lung Cancer Models," PLoS One, 8(6): e65757, p. 1-15 (2013).
Sica et al., "Hypoxia: a double-edged sword of immunity," J Mol Med, 89(7):657-665 (2011).
Sitkovsky et al., "Targeting the Hypoxia-Adenosinergic Signaling Pathway to Improve the Adoptive Immunotherapy of Cancer," J Mol Med, 91: 147-155 (2013).
Vaupel et al., "Tumor hypoxia: causative factors, compensatory mechanisms, and cellular response," Oncologist, 9(Suppl.5):4-9 (2004).
Zhang et al., "Starved and Asphyxiated: How Can CD8+T Cells within a Tumor Microenvironment Prevent Tumor Progression," Front Immunol, 7: 32, p. 1-7 (2016).

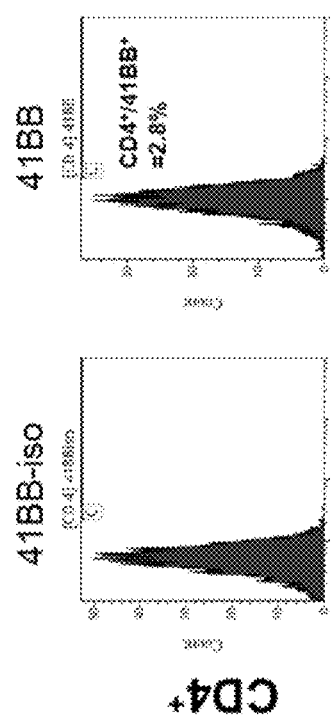
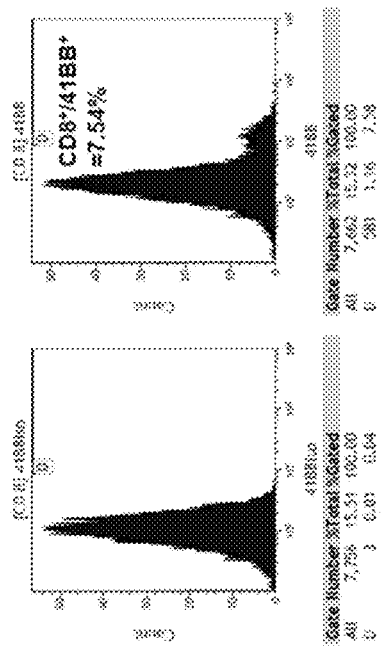
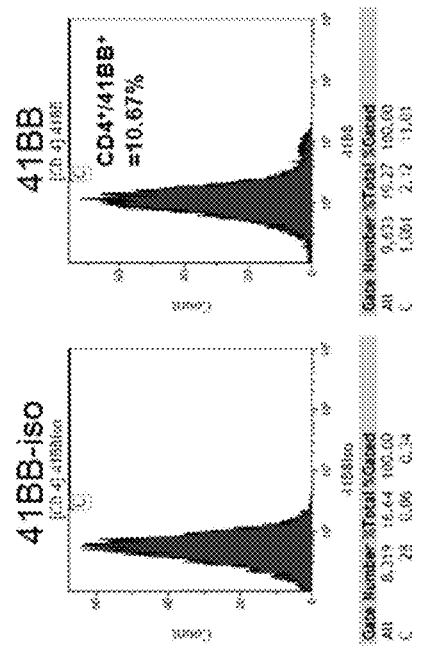
Figure 8 (continued)

ACTIVATION OF MARROW INFILTRATING LYMPHOCYTES IN HYPOXIC ALTERNATING WITH NORMOXIC CONDITIONS

PRIORITY CLAIM

This application is a continuation application of U.S. application Ser. No. 15/112,353, filed Jul. 18, 2016, now U.S. Patent 9,687,510, which is a 371 National Phase Application of PCT Application No. PCT/US2015/048536, filed Sep. 4, 2015, which claims priority to U.S. Provisional Patent Application No. 62/045,782, filed on Sep. 4, 2014, and U.S. Provisional Patent Application No. 62/186,040, filed on Jun. 29, 2015, each of which is hereby incorporated by reference in its entirety.

BACKGROUND

Myeloablative chemotherapy is an accepted therapy for many hematologic malignancies including multiple myeloma albeit with minimal evidence of long-term cures. However, the myeloablative therapy also provides an ideal platform for the superimposition of immune-based therapies. Specifically, the lymphopenia resulting from high dose chemotherapy facilitates homeostatic lymphocytic proliferation, eliminates tolerogenic antigen presenting cells (APCs), and induces cytokine release that generates a more favorable environment for adoptive T cell therapy. Indirect evidence that the immune system can contribute to the clinical benefits of high dose chemotherapy was shown with early lymphoid recovery resulting in improved clinical outcomes in patients with myeloma, lymphoma, and acute myeloid leukemia undergoing an autologous stem cell transplant. Furthermore, these improved outcomes in myeloma correlated directly with the dose of autologous lymphocytes infused from the apheresis product. Taken together, these data support the hypothesis that anti-tumor immunity can have clinically measurable benefits and advances the question of how to harness such immunity to augment the efficacy of currently available therapies.

The ability to eradicate measurable disease with adoptive T cell therapy (ACT) requires T cells to be appropriately activated and present in sufficient numbers, possess appreciable anti-tumor activity, home to the tumor site, effectively kill the tumor upon encounter, and persist over time. Stimulation of T cells with any technique including paramagnetic beads to which anti-CD3 and CD28 are bound can effectively reverse an anergic (tolerant) state, generate activated T cells, and significantly expand their numbers. While bead-bound anti-CD3 and CD28 provide a straightforward and robust T cell amplification in vitro, a major limitation of this approach is the non-specific stimulation of the entire T cell repertoire without enrichment of tumor specific T cells. One strategy to augment the tumor specificity of ACT is to use a T cell population with greater endogenous tumor specificity. Such an enrichment accounts for the considerable anti-tumor activity of ACT using tumor infiltrating lymphocytes (TILs) from metastatic melanoma. However, TILs are present only in a subset of patients with metastatic melanoma, and of those, successful TIL preparations can be achieved in only 60-70% of patients with harvestable tumor, which limits the general applicability of such an approach. Bone marrow is the tumor microenvironment for many hematologic malignancies such as multiple myeloma, and thus, marrow-infiltrating lymphocytes (MILs) could be harnessed to generate tumor specific T cell therapy for these specific cancers. In contrast to TILs, MILs are present in all patients, can be obtained with a simple bed-side procedure, and can be rapidly expanded in all patients.

In hematologic malignancies, the bone marrow represents not only the site of disease but also a unique microenvironment. Even in solid tumors, evidence exists that MILs can be enriched in memory or effector-memory T cells. The immune component within the bone marrow is a reservoir of antigen experienced T cells for both tumor specific T cells in host with early stage breast cancer as well as vaccine-primed T cells. In the bone marrow, memory CD4 cells are maintained through interactions with IL-7 expressing stromal cells and CD8 cells are maintained through the persistence of antigen expression and effective antigen presentation. As such, the heightened tumor specificity of MILs in this setting is likely due to the presence of tumor as a source of antigen while their persistence is maintained through the unique immune interactions with stromal elements, cytokines, and antigen presenting cells capable of effective antigen presentation in this environment.

Ex-vivo activated MILs possess several essential properties for adoptive T cell therapy. Upon activation, they demonstrate significant tumor specificity compared to their peripheral blood lymphocyte counterparts, and they target a broad range of antigens present on both the mature multiple myeloma plasma cells as well as their clonogenic precursors and effectively kill multiple myeloma plasma cells. Similar to TILs, MILs have a greater endogenous polyclonal antigenic specificity than peripheral lymphocytes. In contrast to TILs, MILs are present in all patients and are obtained from a more immune responsive microenvironment. As such, MILs represent a novel and promising tumor-specific approach to ACT for hematologic malignancies with bone marrow involvement.

SUMMARY

In some aspects, the invention relates to a composition comprising marrow infiltrating lymphocytes ("MILs"). The composition may comprise a population of MILs that expresses CD3. For example, at least about 40% of the cells in the composition may be MILs from the population of MILs that expresses CD3. For example, the composition may comprise MILs, and 40% of the cells may express CD3 as determined by a flow cytometry gate; thus, at least about 40% of the cells in the composition would be from the population of MILs that expresses CD3. The composition may comprise a population of MILs that expresses interferon gamma ("IFNγ"). For example, at least about 2% of the cells in the composition may be MILs from the population of MILs that expresses IFNγ. The composition may comprise a population of MILs that expresses CXCR4. For example, at least about 98% of the cells in the composition may be MILs from the population of MILs that expresses CXCR4. The composition may comprise a population of MILs that expresses CD4. The composition may comprise a population of MILs that expresses CD8. The composition may comprise a population of MILs that expresses 4-1BB. For example, at least about 21% of the cells in the composition may be MILs from the population of MILs that expresses 4-1BB.

In some aspects, the invention relates to a method for activating marrow infiltrating lymphocytes ("MILs"), comprising incubating MILs in an environment comprising less than 21% oxygen.

In some aspects, the invention relates to a method for treating cancer in a subject. The method may comprise administering to the subject a composition comprising MILs. In some embodiments, the method comprises removing marrow infiltrating lymphocytes ("MILs") from the subject; and incubating the MILs in an environment comprising less than 21% oxygen, thereby producing activated MILs.

DETAILED DESCRIPTION

Figure 1:
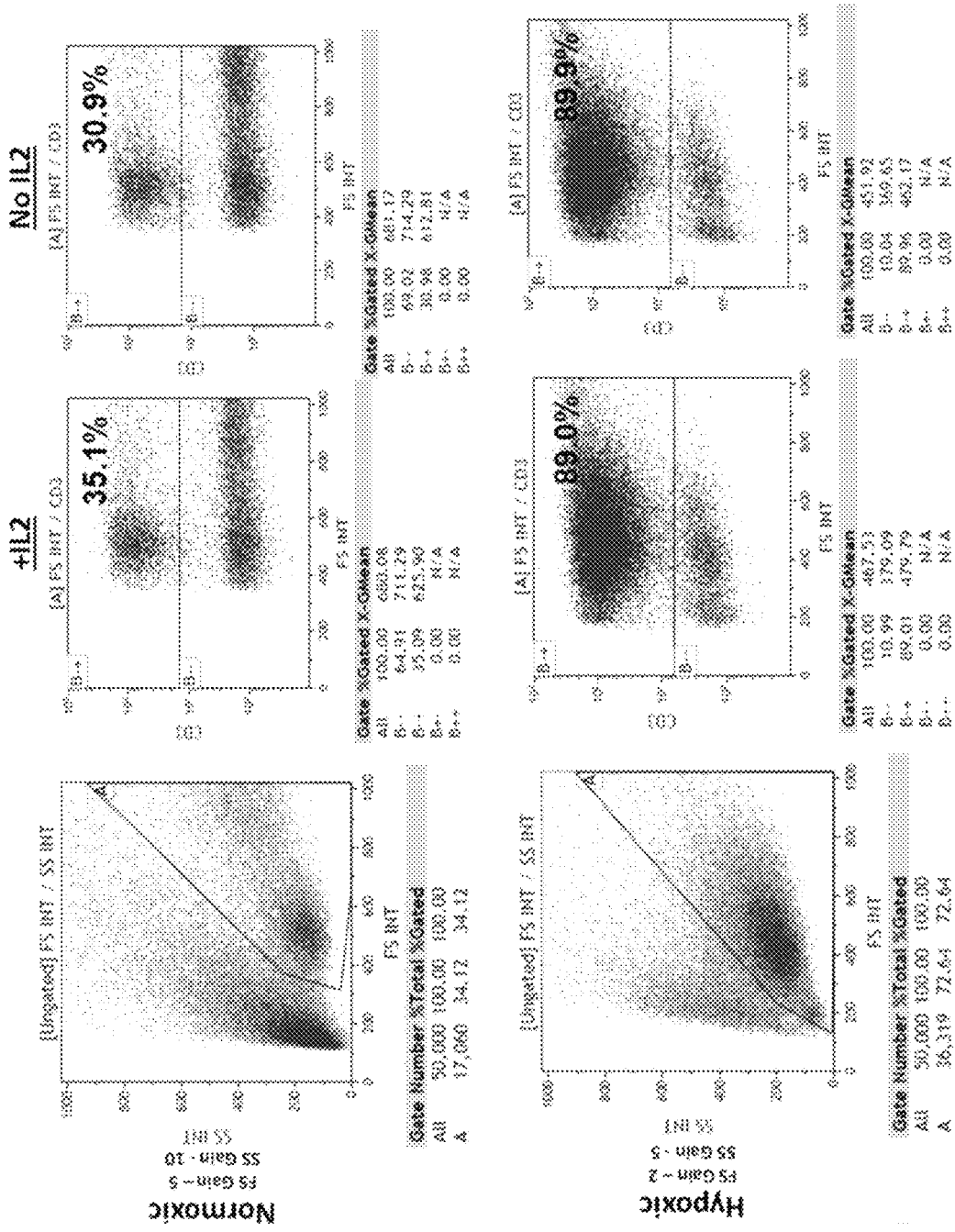
FIG. 1 depicts flow cytometry results for MILs that were expanded under either normoxic conditions or hypoxic conditions in media comprising interleukin 2 (+IL2) or media without interleukin 2 (No IL2). 35.09% of the gated cells grown under normoxic conditions in media comprising interleukin 2 were positive for CD3. 30.98% of the gated cells grown under normoxic conditions in media lacking interleukin 2 were positive for CD3. 89.01% of the gated cells grown under hypoxic conditions in media comprising interleukin 2 were positive for CD3. 89.96% of the gated cells grown under hypoxic conditions in media lacking interleukin 2 were positive for CD3.
Figure 2:
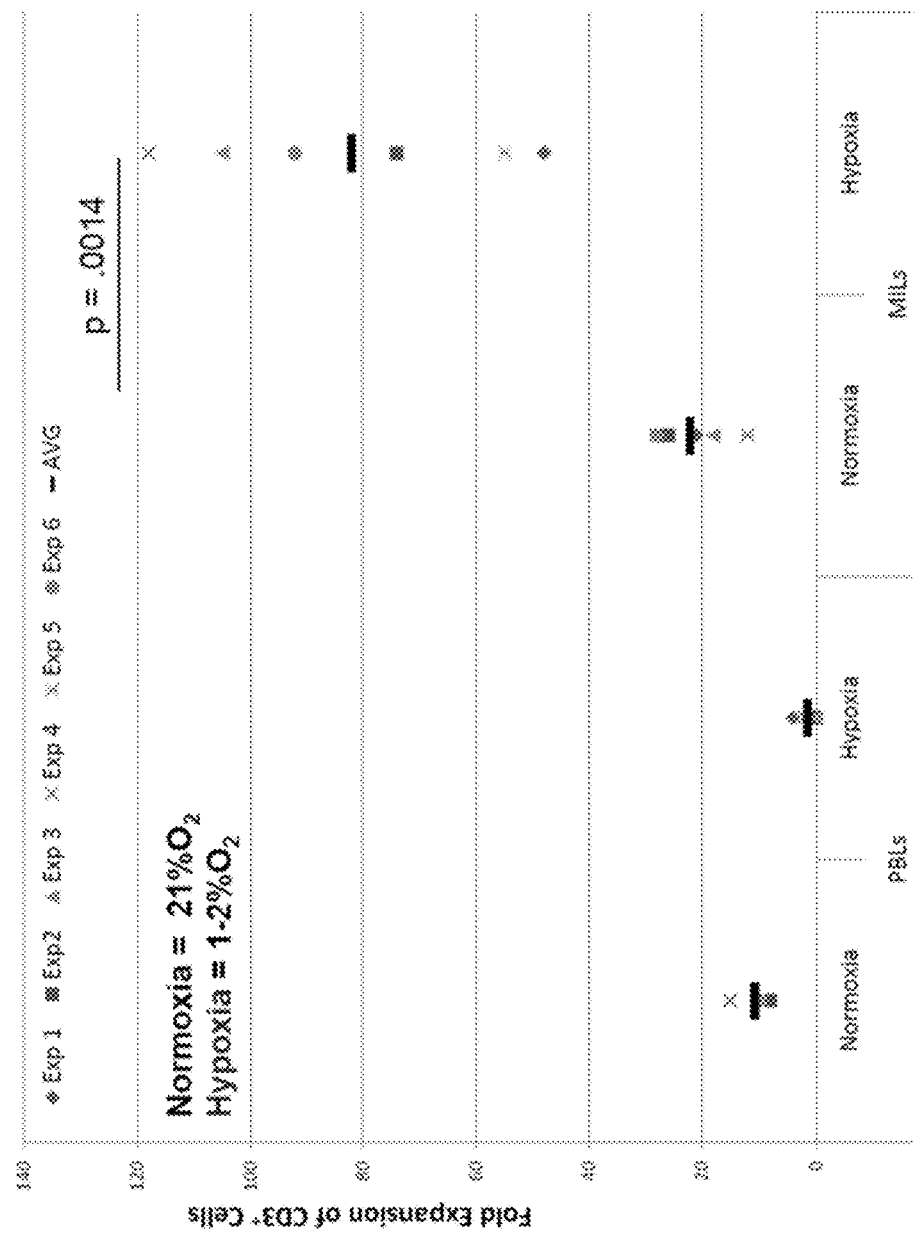
FIG. 2 is a chart showing the expansion of CD3$^+$ cells for peripheral blood lymphocytes (PBLs) and MILs grown under normoxic or hypoxic conditions. Hypoxic conditions decreased the expansion of CD3$^+$ PBLs but increased the expansion of CD3$^+$ MILs.

A major objective to achieve with adoptive T cell therapy is the ability to grow the largest number of tumor specific T cells that will subsequently also expand in vivo upon reinfusion and persist over time. In some aspects, the invention relates to a novel approach to T cell expansion that takes advantage of intrinsic properties of marrow infiltrating lymphocytes ("MILs"). Specifically, MILs significantly differ from peripheral lymphocytes (PBLs). For example, MILs are more easily expanded, upregulate activation markers to a greater extent than PBLs, maintain more of a skewed Vβ repertoire, traffic to the bone marrow, and most importantly, possess significantly greater tumor specificity. MILs anti-myeloma immunity correlates directly with clinical response; however, no in vivo T cell expansion or persistent clinical response has previously been observed following infusion.

Culturing MILs at an $O_2$ level of less than 21% oxygen, such as about 1% oxygen to about 7% oxygen or about 1% oxygen to about 3% oxygen, e.g., 2% oxygen (hypoxic conditions) increases both the overall expansion of the cells as well as their ability to recognize tumor cells relative to culturing in only normoxic conditions. Thus, in some embodiments, the invention relates to a method for the preparation of MILs for therapeutic use comprising one or more of the following. Bone marrow may be collected from a patient. The collected bone marrow may be frozen or immediately used, for example, to create tumor specific MILs. If the bone marrow is frozen, it is preferably thawed before incubation. The bone marrow may be treated to purify MILs through methods known to one of ordinary skill in the art. The MILs may be activated, for example, with beads, e.g., anti-CD3/CD28 beads. The ratio of beads to cells in the solution may vary; in some preferred embodiments, the ratio is 3 to 1. Similarly, the MILs may be expanded in the presence of one or more antibodies, antigens, and/or cytokines, e.g., in the absence of anti-CD3/CD28 beads. The cell count for the collected bone marrow may be determined, for example, to adjust the amount of beads, antibodies, antigens, and/or cytokines to be added to the MILs. In some embodiments, MILs are captured using beads specifically designed to collect the cells.

The collected MILs are preferentially grown in a hypoxic environment, e.g., for a first period of time. In some embodiments, MILs may be placed in a tissue culture bag in X-VIVO™ 15 media supplemented with 2% AB serum and 200U of IL2. It is contemplated that other culture conditions and elements may be used as recognized by a person of ordinary skill in the art. The MILs may be grown in an environment of about 1% to about 7% oxygen (hypoxia; hypoxic conditions), preferably about 1% to about 3% oxygen, such as about 2% oxygen, for about 3 to about 20 days (i.e., a first period of time), such as about 3 to about 10 days, such as 4 days. The hypoxic environment may be created, for example, by adding nitrous oxide to the container in which the cells are grown. In some embodiments, the hypoxic environment may be created by utilizing a hypobaric chamber. After the hypoxic growth, the MILs may be grown in a normoxic environment, e.g., 21% oxygen. In some preferred embodiments, the MILs are grown in normoxic conditions for an additional about 3 to about 7 days (i.e., a second period of time), e.g., for a total of about 3 to about 27 days of growth, such as about 3 to about 10 days growth. The grown cells may then be either administered to a patient (e.g., either the patient or an allogenic recipient) or stored for future use.

MILs collected from the patient's bone marrow and treated in accordance with a method described herein, namely, under hypoxic conditions for a first period of time followed by normoxic conditions for a second period of time, perform unexpectedly better than peripheral blood lymphocytes (PBLs) subjected to the same procedure. The enhanced abilities of the MILs, as shown below, include marked expansion both in vitro and in vivo, enhanced expression of biological markers such as 4-1BB, and increased tumor specificity.

A person of ordinary skill in the art would recognize that the procedure of the present invention can be utilized to treat many different types of cancer, including, myeloma, lung cancer, and breast cancer. As bone marrow is a reservoir of central memory cells, tumor specific T cells from any variety of cancers have been found in the bone marrow of patients. As disclosed herein, hypoxic culturing conditions increase both expansion as well as tumor specificity, and thus, this approach may be used to grow MILs from a wide range of cancer patients. In some preferred embodiments, a patient's MILs are collected, expanded in hypoxic conditions for a first period of time, e.g., for about 1 day to about 20 days, and then expanded in normoxic conditions for a second period of time, e.g., about 3 days to about 7 days. The cells may then be provided to the patient for treatment or stored for future use.

Figure 4:
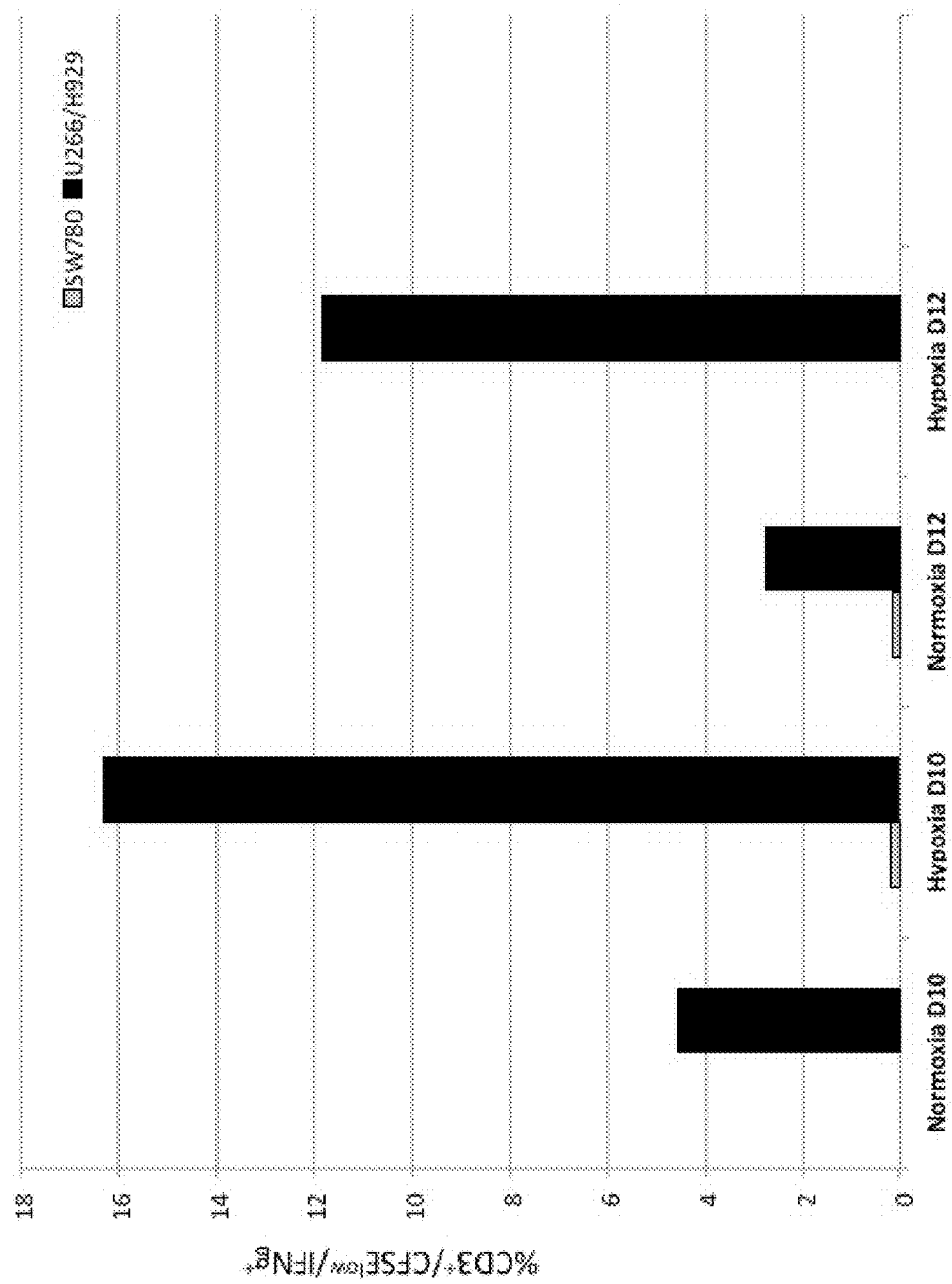
FIG. 4 is a graph depicting the tumor specificity of MILs expanded under hypoxic or normoxic conditions for either myeloma cell lines (U266/H929) or a control cell line (SW780), for cells that were expanded for either 10 days (D10) or for 12 days (D12). Hypoxic cells were grown for 3 days in an environment comprising 2% oxygen, followed by expansion in a normoxic environment (21% oxygen). On day 10, 4% of the cells expanded under normoxic conditions were tumor specific as compared to 25.1% of MILs expanded under hypoxic conditions as determined by the percent of total T cells that were CFSE low and producing interferon gamma (IFNγ) in response to tumor antigen.
Figure 5:
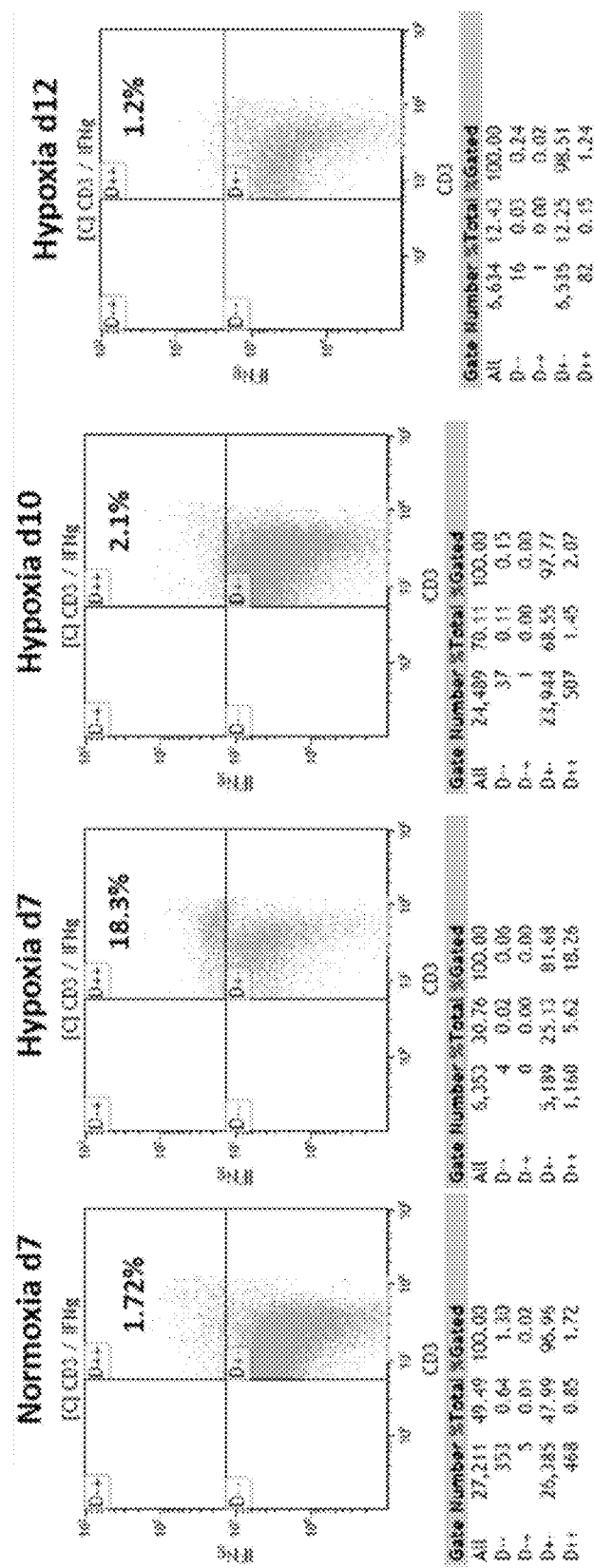
FIG. 5 depicts flow cytometry results for tumor specificity of MILs expanded under various conditions utilizing gates for CD3 and INFγ. After seven days of expansion, 18.26% of MILs grown under hypoxic conditions were positive for both CD3 and interferon gamma. In contrast, only 1.72% of MILs grown under normoxic conditions were positive for both CD3 and interferon gamma.

In some aspects, the invention relates to the finding that expanding MILs in a hypoxic environment allows for in vivo T cell expansion following infusion. Specifically, MILs were grown in 2% $O_2$ (hypoxia) for 3 days followed by a switch to 21% $O_2$ (normoxia), resulting in almost a 10-fold greater tumor specificity (FIG. 4). Taken together, these data suggest that such growth conditions are capable of increasing the absolute number of tumor specific MILs obtained from the same source relative to MILs that a grown under only normoxic conditions.

Figure 3:
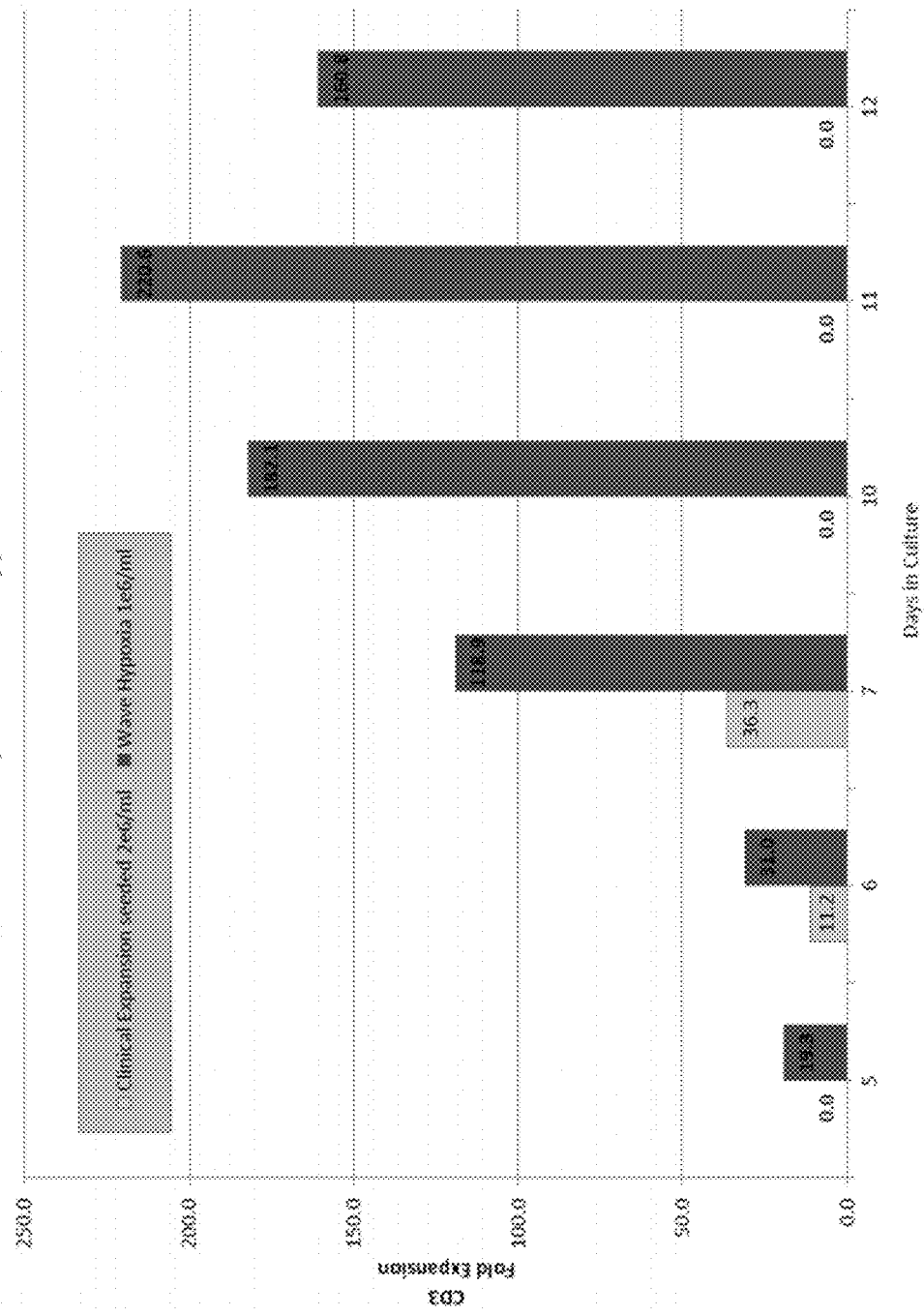
FIG. 3 is a graph comparing the expansion of CD3$^+$ MILs after various time periods of incubation in either normoxic or hypoxic environments. Substantial expansion was observed after 7 days of incubation in a hypoxic environment compared to normoxia, and a CD3$^+$ expansion peaked at 11 days of incubation.

All experiments were performed using MILs products from patient samples. As shown in FIG. 3, expansion of a full scale clinical MILs product in hypoxic conditions dramatically increased T cell numbers. It should be noted that with normoxic conditions, it was difficult to expand MILs past 7 days. In this experiment, the day-7 expansion was 36.3 fold in normoxia versus 119 fold in hypoxia. Furthermore, the cells grown under hypoxic conditions continued to expand up to 12 days and reached a total 220-fold expansion at 11 days.

Figure 8:
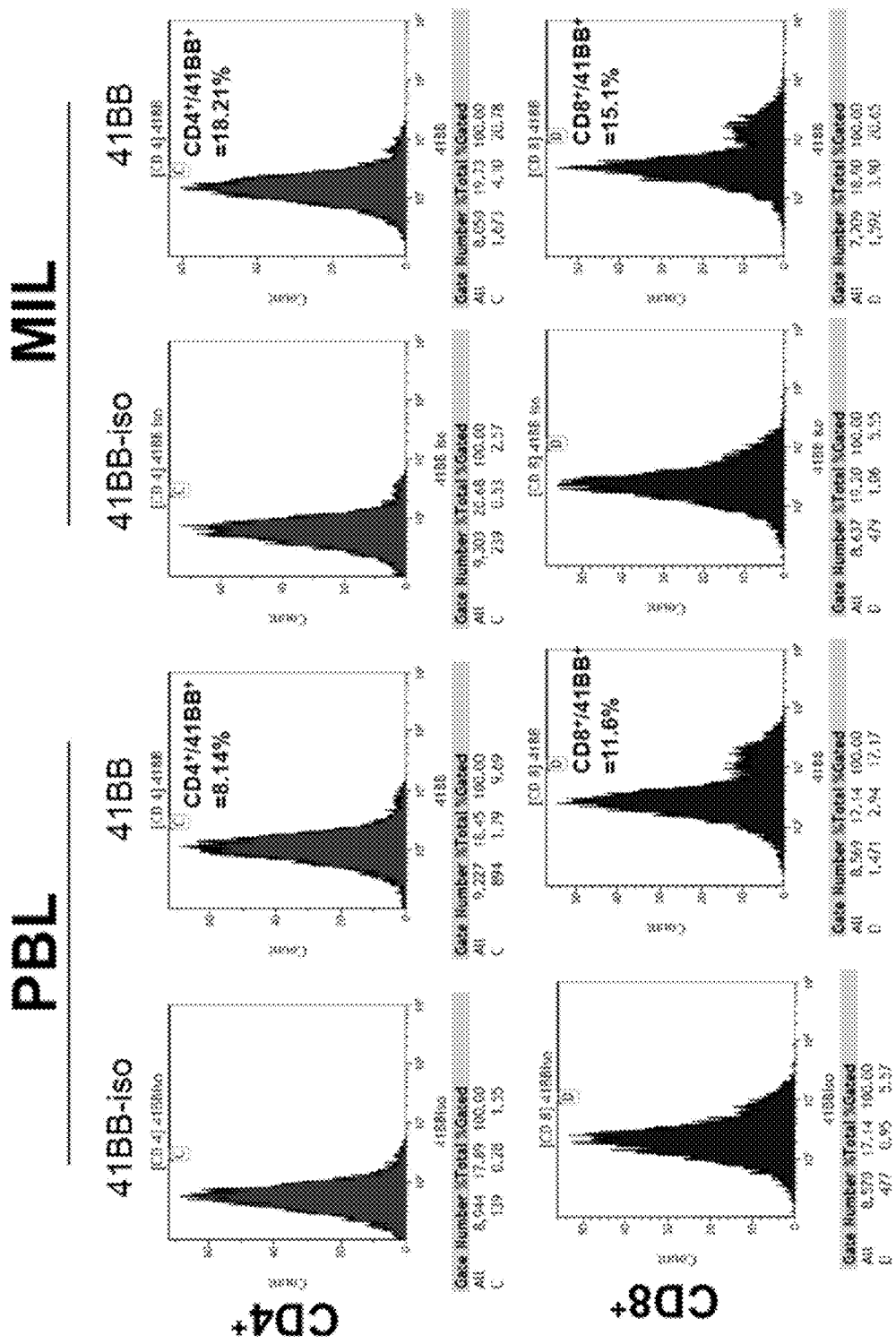
FIG. 8 consists of three panels, labeled panels (A), (B), and (C). Panel A depicts flow cytometry results for peripheral blood lymphocytes (PBL) and MILs prior to cell expansion, utilizing gates for CD4, CD8, and 4-1BB. Panel B depicts flow cytometry results for PBLs and MILs following expansion under normoxic conditions, utilizing gates for CD4, CD8, and 4-1BB. As shown, 4-1BB expression in PBLs decreased in CD8 PBLs, from 11.34% to 0.34%, and MILs CD8 showed a decrease from 15.1% to 7.54%. Panel C depicts flow cytometry results for PBLs and MILs following expansion under hypoxic conditions, utilizing gates for CD4, CD8, and 4-1BB. PBLs downregulated 4-1BB following expansion under hypoxic conditions (CD8 PBLs: baseline 11.34% to 0%), whereas MILs upregulated 4-1BB following expansion under hypoxic conditions (CD8 MILs: baseline 15.1% to 21.79%).
Figure 8:
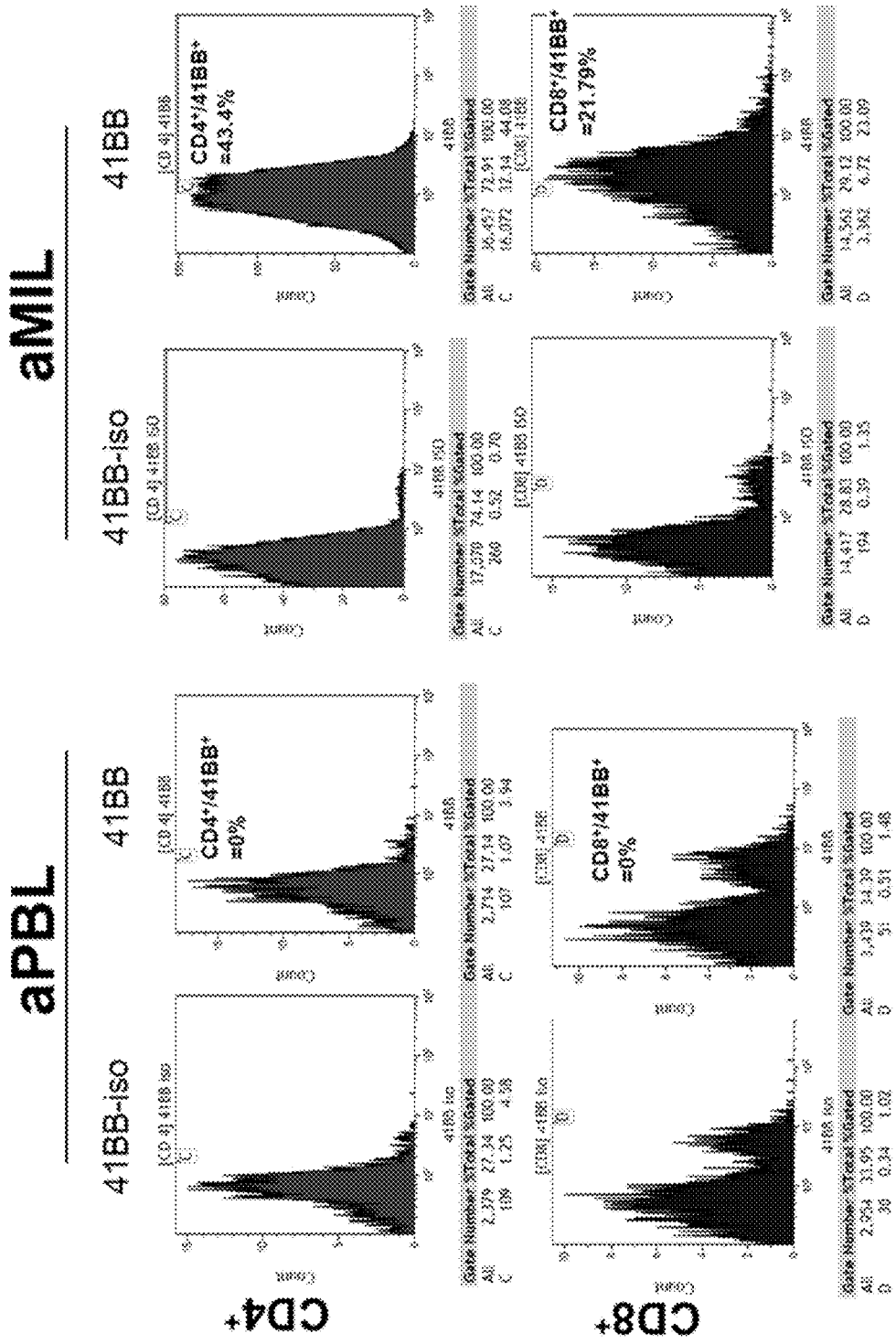

In addition to obtaining better expansions and greater tumor specificity, growth conditions were optimized to maximize T cell survival. Expression of 4-1BB has been shown to be a key regulator of many of these properties. It can regulate T cell expansion, reduce apoptosis, augment the cytotoxic activity of CD8 cells, and enhance survival. Taken together, 4-1BB expression on activated MILs may be an important regulator of heightened survival and tumor specificity. Thus 4-1BB expression was examined on MILs and compared to that on PBLs grown in various conditions. As shown in FIG. 8, the baseline expression of 4-1BB was greater in MILs than PBLs (18.2% v 8.1%). Interestingly, T cell expansion in normoxia reduced its expression in both populations (MILs 10.7%, PBLs 2.8%) whereas expansion in hypoxia significantly increase 4-1BB expression in MILs (43.4%) and completely abrogated its expression in PBLs (0%). These data again underscore the significant differences between PBLs and MIL also demonstrate that 4-1BB upregulation depends upon more factors than simply hypoxic growth conditions.

These culture conditions have been adopted to a clinical trial, and hypoxic growth conditions increased the total T cell expansion from an average of 7.9E9 to 1.8E10. Furthermore, hypoxic growth conditions also enabled the observation of in vivo T cell expansion (FIG. 6, which depicts the total lymphocyte counts through day 60 for all patients).

In some aspects, the invention relates to a composition comprising marrow infiltrating lymphocytes ("MILs"). The MILs may be activated MILs.

In preferred embodiments, the composition comprises a population of MILs that expresses CD3, i.e., wherein each cell in the population of MILs that expresses CD3 is a marrow infiltrating lymphocyte that expresses CD3, e.g., as detected by flow cytometry. For example, at least about 40% of the cells in the composition may be MILs from the population of MILs that express CD3, such as at least about 45%, 50%, 55%, 60%, 65%, 70%, 75%, 80%, 85%, 86%, 87%, 88%, or even at least about 89% of the cells in the composition. In one preferred embodiment, at least about 80% of the cells in the composition may be MILs from the population of MILs that express CD3. In some embodiments, about 40% to about 100% of the cells in the composition may be MILs from the population of MILs that express CD3, such as about 45% to about 100%, about 50% to about 100%, about 55% to about 100%, about 60% to about 100%, about 65% to about 100%, about 70% to about 100%, about 75% to about 100%, about 80% to about 100%, about 85% to about 100%, about 86% to about 100%, about 87% to about 100%, about 88% to about 100%, or even about 89% to about 100% of the cells in the composition. In some embodiments, the composition comprises either a population of MILs that do not express CD3, e.g., as detected by flow cytometry, or a population of MILs that expresses low levels of CD3, i.e., relative to the expression level of MILs from the population of MILs that express CD3.

In some embodiments, the composition comprises a population of MILs that expresses interferon gamma ("IFNγ"), i.e., wherein each cell in the population of MILs that expresses IFNγ is a marrow infiltrating lymphocyte that expresses IFNγ, e.g., as detected by flow cytometry. For example, at least about 2% of the cells in the composition may be MILs from the population of MILs that express IFNγ, such as at least about 2%, 3%, 4%, 5%, 6%, 7%, 8%, 9%, 10%, 11%, 12%, 13%, 14%, 15%, 16%, 17%, or even at least about 18% of the cells in the composition. In some embodiments, about 2% to about 100% of the cells in the composition may be MILs from the population of MILs that express IFNγ, such as about 2% to about 100%, about 3% to about 100%, about 4% to about 100%, about 5% to about 100%, about 6% to about 100%, about 7% to about 100%, about 8% to about 100%, about 9% to about 100%, about 10% to about 100%, about 11% to about 100%, about 12% to about 100%, about 13% to about 100%, about 14% to about 100%, about 15% to about 100%, about 16% to about 100%, about 17% to about 100%, or even about 18% to about 100% of the cells in the composition. In some embodiments, the composition comprises either a population of MILs that do not express IFNγ, e.g., as detected by flow cytometry, or a population of MILs that expresses low levels of IFNγ, i.e., relative to the expression level of MILs from the population of MILs that express IFNγ.

In some embodiments, the composition comprises a population of MILs that expresses CXCR4, i.e., wherein each cell in the population of MILs that expresses CXCR4 is a marrow infiltrating lymphocyte that expresses CXCR4, e.g., as detected by flow cytometry. For example, at least about 98% of the cells in the composition may be MILs from the population of MILs that express CXCR4, such as at least about 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, or even at least about 99.7% of the cells in the composition. In some embodiments, about 98% to about 100% of the cells in the composition may be MILs from the population of MILs that express CXCR4, such as at least about 98.1% to about 100%, about 98.2% to about 100%, about 98.3% to about 100%, about 98.4% to about 100%, about 98.5% to about 100%, about 98.6% to about 100%, about 98.7% to about 100%, about 98.8% to about 100%, about 98.9% to about 100%, about 99.0% to about 100%, about 99.1% to about 100%, about 99.2% to about 100%, about 99.3% to about 100%, about 99.4% to about 100%, about 99.5% to about 100%, about 99.6% to about 100%, or even about 99.7% to about 100% of the cells in the composition. In some embodiments, the composition comprises either a population of MILs that do not express CXCR4, e.g., as detected by flow cytometry, or a population of MILs that expresses low levels of CXCR4, i.e., relative to the expression level of MILs from the population of MILs that express CXCR4.

In some embodiments, the composition comprises a population of MILs that expresses CD4. The population of MILs that expresses CD4 may comprise a plurality of MILs that expresses CXCR4.

The population of MILs that expresses CD4 may comprise a plurality of MILs that expresses 4-1BB. For example, at least about 21% of the cells in the composition may be MILs from the plurality of MILs that expresses 4-1BB, such as at least about 22%, 23%, 24%, 25%, 26%, 27%, 28%, 29%, 30%, 31%, 32%, 33%, 34%, 35%, 36%, 37%, 38%, 39%, 40%, 41%, 42%, or even at least about 43% of the cells in the composition. In some embodiments, about 21% to about 100% of the cells in the composition may be MILs from the plurality of MILs that expresses 4-1BB, such as about 22% to about 100%, about 23% to about 100%, about 24% to about 100%, about 25% to about 100%, about 26% to about 100%, about 27% to about 100%, about 28% to about 100%, about 29% to about 100%, about 30% to about 100%, about 31% to about 100%, about 32% to about 100%, about 33% to about 100%, about 34% to about 100%, about 35% to about 100%, about 36% to about 100%, about 37% to about 100%, about 38% to about 100%, about 39% to about 100%, about 40% to about 100%, about 41% to about 100%, about 42% to about 100%, or even about 43% to about 100% of the cells in the composition.

The composition may comprise a population of MILs that expresses CD8. The population of MILs that expresses CD8 may comprise a plurality of MILs that expresses CXCR4.

The population of MILs that expresses CD8 may comprise a plurality of MILs that expresses 4-1BB. For example, at least about 21% of the cells in the composition may be MILs from the plurality of MILs that expresses 4-1BB, such as at least about 8%, 9%, 10%, 11%, 12%, 13%, 14%, 15%, 16%, 17%, 18%, 19%, 20% or even at least about 21% of the cells in the composition. In some embodiments, about 2% to about 100% of the cells in the composition may be MILs from the plurality of MILs that expresses 4-1BB, such as about 8% to about 100%, about 9% to about 100%, about 10% to about 100%, about 11% to about 100%, about 12% to about 100%, about 13% to about 100%, about 14% to about 100%, about 15% to about 100%, about 16% to about 100%, about 17% to about 100%, about 18% to about 100%, about 19% to about 100%, about 20% to about 100%, or even about 21% to about 100% of the cells in the composition.

In some embodiments, the composition comprises a population of MILs that expresses 4-1BB. For example, at least about 21% of the cells in the composition may be MILs from the population of MILs that expresses 4-1BB, such as at least about 22%, 23%, 24%, 25%, 26%, 27%, 28%, 29%, 30%, 31%, 32%, 33%, 34%, 35%, 36%, 37%, 38%, 39%, 40%, 41%, 42%, or even at least about 43% of the cells in the composition. In some embodiments, about 21% to 100% of the cells in the composition may be MILs from the population of MILs that expresses 4-1BB, such as about 22% to about 100%, about 23% to about 100%, about 24% to about 100%, about 25% to about 100%, about 26% to about 100%, about 27% to about 100%, about 28% to about 100%, about 29% to about 100%, about 30% to about 100%, about 31% to about 100%, about 32% to about 100%, about 33% to about 100%, about 34% to about 100%, about 35% to about 100%, about 36% to about 100%, about 37% to about 100%, about 38% to about 100%, about 39% to about 100%, about 40% to about 100%, about 41% to about 100%, about 42% to about 100%, or even about 43% to about 100% of the cells in the composition. In some embodiments, the composition comprises either a population of MILs that do not express 4-1BB, e.g., as detected by flow cytometry, or a population of MILs that expresses low levels of 4-1BB, i.e., relative to the expression level of MILs from the population of MILs that express 4-1BB.

In some aspects, the invention relates to a method for preventing or treating cancer in a subject, comprising administering to the subject any one of the compositions described herein. In preferred embodiments, the method comprises administering to the subject a therapeutically-effective amount of any one of the compositions described herein. In preferred embodiments, the method comprises administering to the subject a therapeutically-effective amount of MILs, e.g., activated MILs, as described herein. The subject may have a neoplasm, such as cancer. For example, the subject may have multiple myeloma. The subject may be a human subject.

In some aspects, the invention relates to a method for making a composition as described herein, comprising incubating MILs in a hypoxic environment. In some aspects, the invention relates to a method for activating marrow infiltrating lymphocytes ("MILs"), comprising incubating MILs in a hypoxic environment.

In some aspects, the invention relates to a method for method for treating cancer in a subject. The method may comprise removing marrow infiltrating lymphocytes ("MILs") from the subject; incubating the MILs in a hypoxic environment, thereby producing activated MILs; and administering the activated MILs to the subject.

The hypoxic environment may comprise less than about 21% oxygen, such as less than about 20%, 19%, 18%, 17%, 16%, 15%, 14%, 13%, 12%, 11%, 10%, 9%, 8%, 7%, 6%, 5%, 4%, or less than about 3% oxygen. For example, the hypoxic environment may comprise about 0% oxygen to about 20% oxygen, such as about 0% oxygen to about 19% oxygen, about 0% oxygen to about 18% oxygen, about 0% oxygen to about 17% oxygen, about 0% oxygen to about 16% oxygen, about 0% oxygen to about 15% oxygen, about 0% oxygen to about 14% oxygen, about 0% oxygen to about 13% oxygen, about 0% oxygen to about 12% oxygen, about 0% oxygen to about 11% oxygen, about 0% oxygen to about 10% oxygen, about 0% oxygen to about 9% oxygen, about 0% oxygen to about 8% oxygen, about 0% oxygen to about 7% oxygen, about 0% oxygen to about 6% oxygen, about 0% oxygen to about 5% oxygen, about 0% oxygen to about 4% oxygen, or about 0% oxygen to about 3% oxygen. In preferred embodiments, the hypoxic environment comprises about 1% to about 7% oxygen. The hypoxic environment may comprise about 20%, 19%, 18%, 17%, 16%, 15%, 14%, 13%, 12%, 11%, 10%, 9%, 8%, 7%, 6%, 5%, 4%, 3%, 2%, 1%, or about 0% oxygen. In preferred embodiments, the hypoxic environment comprises about 7%, 6%, 5%, 4%, 3%, 2%, or 1% oxygen.

Incubating MILs in a hypoxic environment may comprise incubating the MILs, e.g., in tissue culture medium, for at least about 1 hour, such as at least about 12 hours, 18 hours, 24 hours, 30 hours, 36 hours, 42 hours, 48 hours, 60 hours, 3 days, 4 days, 5 days, 6 days, 7 days, 8 days, 9 days, 10 days, 11 days, 12 days, 13 days, or even at least about 14 days. Incubating may comprise incubating the MILs for about 1 hour to about 30 days, such as about 1 day to about 20 days, about 1 day to about 14 days, or about 1 day to about 12 days. In some preferred embodiments, incubating MILs in a hypoxic environment comprises incubating the MILs in a hypoxic environment for about 2 days to about 5 days. The method may comprise incubating MILs in a hypoxic environment for about 1 day, 2 days, 3 days, 4 days, 5 days, 6 days, 7 days, 8 day, 9 days, 10 days, 11 days, 12 days, 13 days, or 14 days. In some preferred embodiments, the method comprises incubating the MILs in a hypoxic environment for about 3 days.

In preferred embodiments, the method further comprises incubating the MILs in a normoxic environment, e.g., after incubating the MILs in a hypoxic environment.

The normoxic environment may comprise at least about 21% oxygen. The normoxic environment may comprise about 5% oxygen to about 30% oxygen, such as about 10% oxygen to about 30% oxygen, about 15% oxygen to about 25% oxygen, about 18% oxygen to about 24% oxygen, about 19% oxygen to about 23% oxygen, or about 20% oxygen to about 22% oxygen. In some embodiments, the normoxic environment comprises about 21% oxygen.

Incubating MILs in a normoxic environment may comprise incubating the MILs, e.g., in tissue culture medium, for at least about 1 hour, such as at least about 12 hours, 18 hours, 24 hours, 30 hours, 36 hours, 42 hours, 48 hours, 60 hours, 3 days, 4 days, 5 days, 6 days, 7 days, 8 days, 9 days, 10 days, 11 days, 12 days, 13 days, or even at least about 14 days. Incubating may comprise incubating the MILs for about 1 hour to about 30 days, such as about 1 day to about 20 days, about 1 day to about 14 days, about 1 day to about 12 days, or about 2 days to about 12 days.

EXEMPLIFICATION

Example 1

Activation and Expansion of T Cells in Hypoxic and Normoxic Environments

Bone marrow (BM) T cell numbers are determined using flow cytometry. Anti-CD3/anti-CD28 beads are added at the pre-determined ratio (beads:CD3 cell) in media with recombinant human cytokines at a predetermined concentration. Cells are plated in a plate, flask, or bag. Hypoxic conditions are achieved by flushing either the hypoxic chamber or cell culture bag for 3 minutes with a 95% Nitrogen and 5% $CO_2$ gas mixture. The receptacle is then filled with this gas mixture for 30 seconds. This leads to a 2% or less $O_2$ gas in the receptacle. Cells are cultured at 37 C for 3 or more days and the hypoxic air is released and replaced with normoxic (21% atmospheric oxygen) levels.

Example 2

Phenotypic Determination of Cell Types

Cells are stained with flurochrome conjugated antibodies for the desired determination. CD3, CD4, CD8, CXCR4, 41BB, CD27, CD28, CTLA-4, PD-1, CD45RO, CD62L, CD95, IFNg, IL17, live/dead dye, and/or other antibodies of interest that are directly conjugated to flurochromes are used with appropriate isotype controls. Briefly, $1 \times 10^6$ cells or less are washed with FACS buffer (1XHBSS/2% FBS/0.5% EDTA/0.5% NaAzide) or similar wash buffer in either a plate or a tube by spinning in a centrifuge. The wash buffer is removed and antibodies and isotype controls are added at predetermined concentrations. The cells are stained between 7-30 minutes at either room temperature or at 4° C. The cells are washed 2× with wash buffer and re-suspended in minimal wash buffer. The cells are then run on a flow cytometer that has been properly compensated and prepared for the flurochromes that are being utilized. 10,000 or greater numbers of events are collected for each sample. Data is analyzed utilizing FACS analysis software. Flurochrome labelled cells are compared to isotype controls for back ground removal. Data is graphed as % positive-% background.

Example 3

Determination of Fold Expansion

Bone marrow cells are enumerated at the beginning of expansion. The percentage of CD3+ cells is determined utilizing flow cytometry. The total number of CD3+ MILs is determined by multiplying the total number of cells with the percentage of CD3=total number of CD3+ MILs in culture. On the final day of culture the cells are harvested and counted (both manually and with an automated cell counter). The percentage of CD3+ is determined. The total number of CD3+ cells on the final day of culture is determined by multiplying total cell number with the percentage of CD+=total number of CD3+ MILs harvested. Total fold expansion=Total number of CD3+ MILs harvested on the final day of culture divided by the total number of CD3+ MILs on the initial day of culture.

Example 4

Tumor Specificity

MILs are labelled with CFSE or a similar cell membrane integration dye according to the manufacturers' protocol. Autologous BM is pulsed with either media alone, a negative control (unrelated protein or lysate) or with the protein or lysate of interest. CFSE labelled cells are then co-cultured with pulsed autologous BM for 2-7 days. Cells are harvested from the tissue culture plate or flask and then stained with CD3 extracellularly and intracellularly with IFNg. Analysis of tumor specificity is determined by gating on CD3+ cells that are CFSE low (divided cells) and that are producing IFNg.

Example 5

Activation and Expansion of T Cells in Hypoxic and Normoxic Environments

Figure 9:
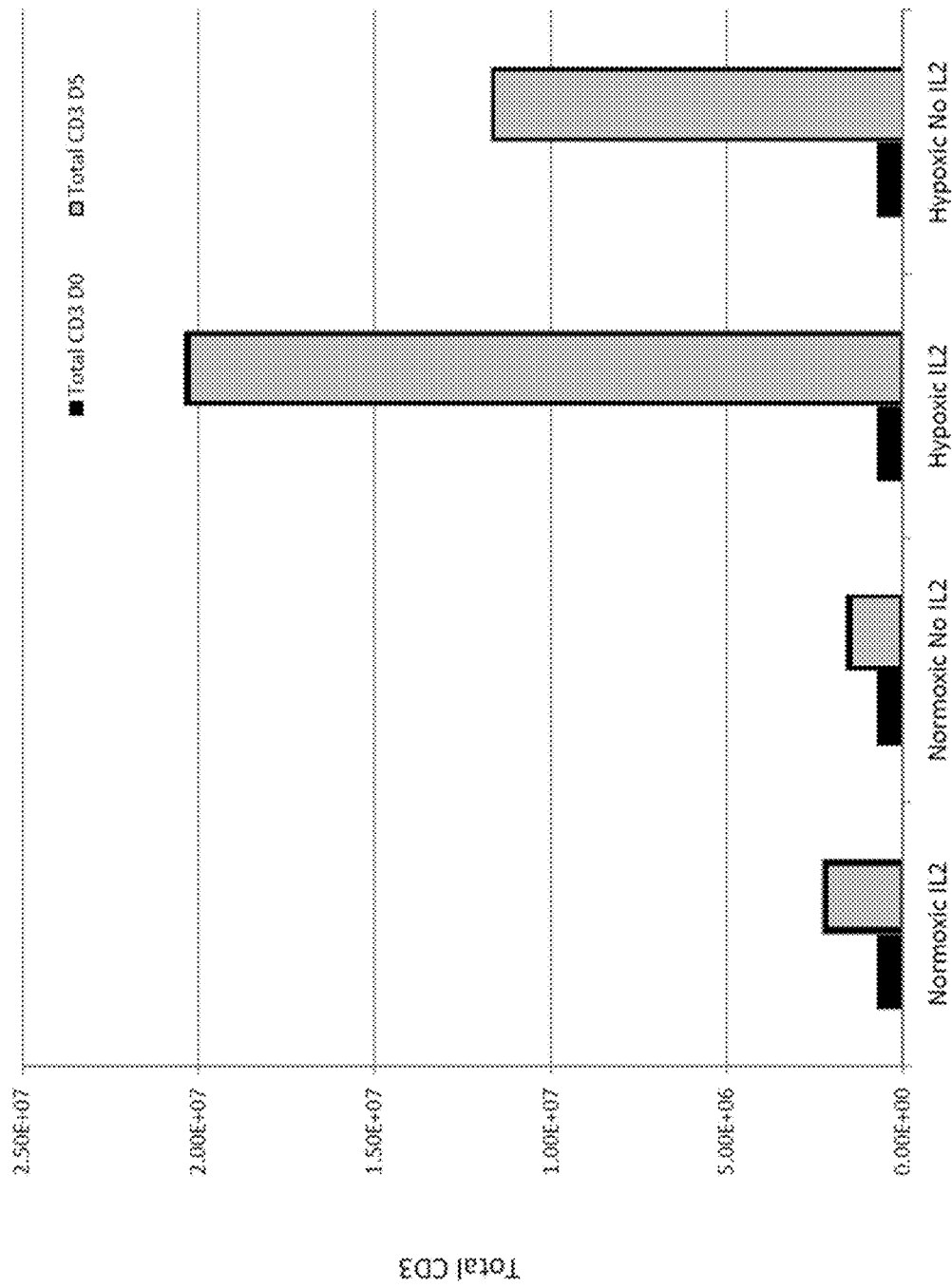
FIG. 9 is a graph that shows that the growth of MILs under hypoxic conditions increases the number of CD3$^+$ cells relative to growth under only normoxic conditions.

MILs were grown in 2% $O_2$ (hypoxia) for 3 days followed by a switch to 21% $O_2$ (normoxia) for an additional 5 days in the presence or absence of IL-2. As shown in FIG. 9, growth in hypoxia followed by normoxia resulted in almost a 10-fold increase in expansion as compared to MILs grown exclusively in normoxic conditions. Tumor specificity was also markedly enhanced as shown on FIG. 4. On day 10, 4% of CFSE-low cells were tumor specific in normoxic conditions as opposed to 25.1% for MILs grown in hypoxic conditions. Taken together, these data suggest that these growth conditions are capable of increasing the absolute number of tumor specific upon activation.

The experiments in the preceding paragraph were performed on a small sample. MILs product from a patient in a first clinical study was also expanded using this method. As shown in FIG. 3, expansion of MILs in these conditions dramatically increased T cell numbers. Growth in normoxic conditions was seldom capable of expanding MILs past 7 days. In this experiment, the day-7 fold expansion was 36.3 fold in normoxic conditions as oppose to 119 in hypoxic conditions. Furthermore, the cells continued to expand up to 12 days and reached a total 220-fold expansion at 11 days before beginning to die.

Figure 10:
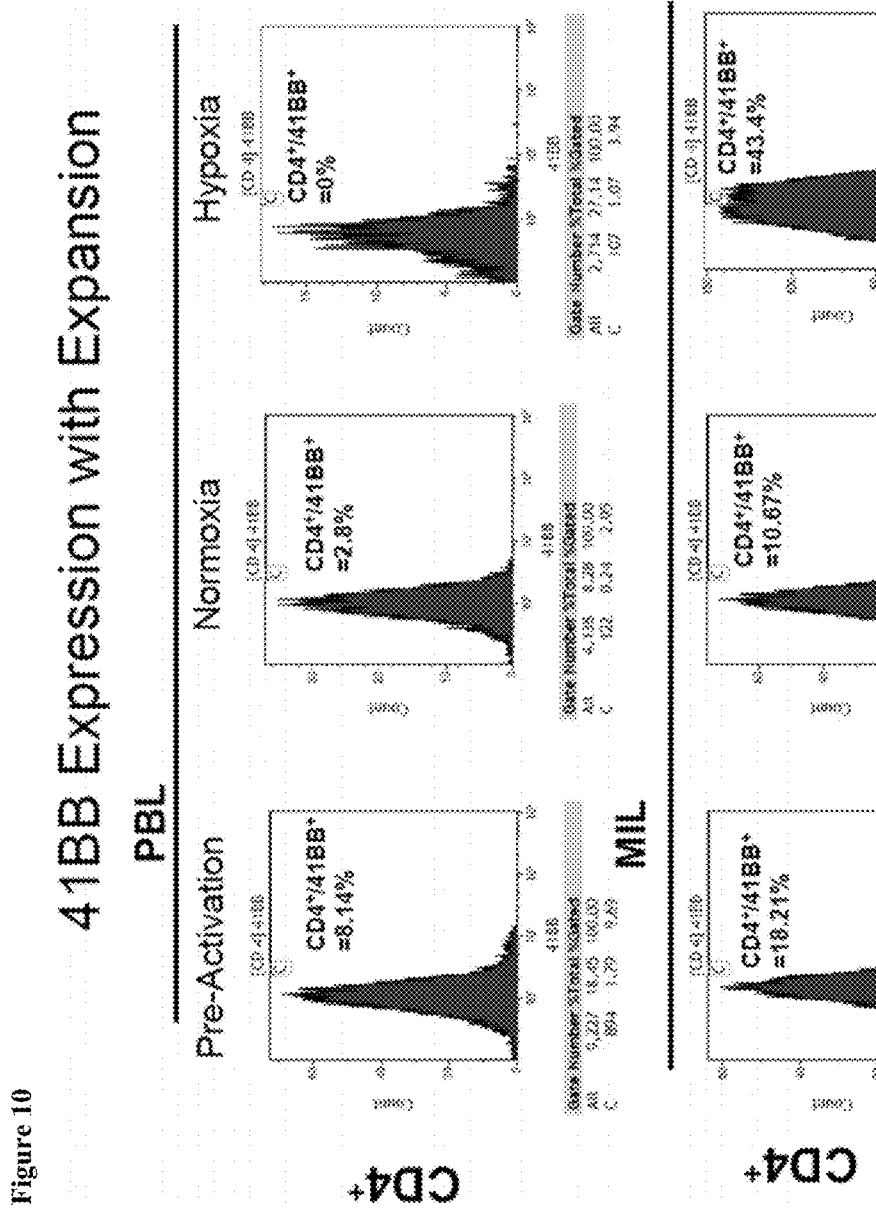
FIG. 10 shows flow cytometry results indicating that the expansion of MILs under hypoxic conditions results in a higher percentage of CD4$^+$/4-1BB$^+$ cells than either expansion of PBLs under hypoxic conditions or the expansion of MILs under normoxic conditions.

Expression of 4-1BB has been shown to be a key regulator of many of these properties. It can regulate T cell expansion, reduce apoptosis, augment the cytotoxic activity of CD8 cells and enhances survival. Furthermore, HIF1α regulates survival of antigen-driven T cells. Chimeric antigen receptor (CAR) modified T cells with the vector expressing 4-1BB have shown significant in vivo expansion. Taken together, 4-1BB expression on activated MILs can be an important regulator of heightened survival and tumor specificity. One marked advantage of the method disclosed herein is that there is no need to modify the MILs in order to achieve 4-1BB enhanced expression. This advantage is shown in FIG. 10 where MILs or PBLs were grown in either normoxic or hypoxic conditions. Baseline expression of 4-1BB was evaluated in MILs and compared to PBLs. As shown, 4-1BB expression was greater in MILs than PBLs (18.2% v 8.1%). Interestingly, T cell expansion in normoxia reduced its expression in both populations (MILs 10.7%, PBLs 2.8%) whereas expansion in hypoxia significantly increases 4-1BB expression in MILs (43.4%) and completely abrogated its expression in PBLs (0%). These data again underscore the significant differences between PBLs and MIL also demonstrates that 4-1BB upregulation depends upon more factors than simply hypoxic growth conditions. More importantly, the unexpected upregulation of 4-1BB demonstrates that the method of the present invention makes a significant difference in the treatment of patients using hypoxically grown MILs. Similar results were observed with CD8 cells (FIG. 8).

Figure 6:
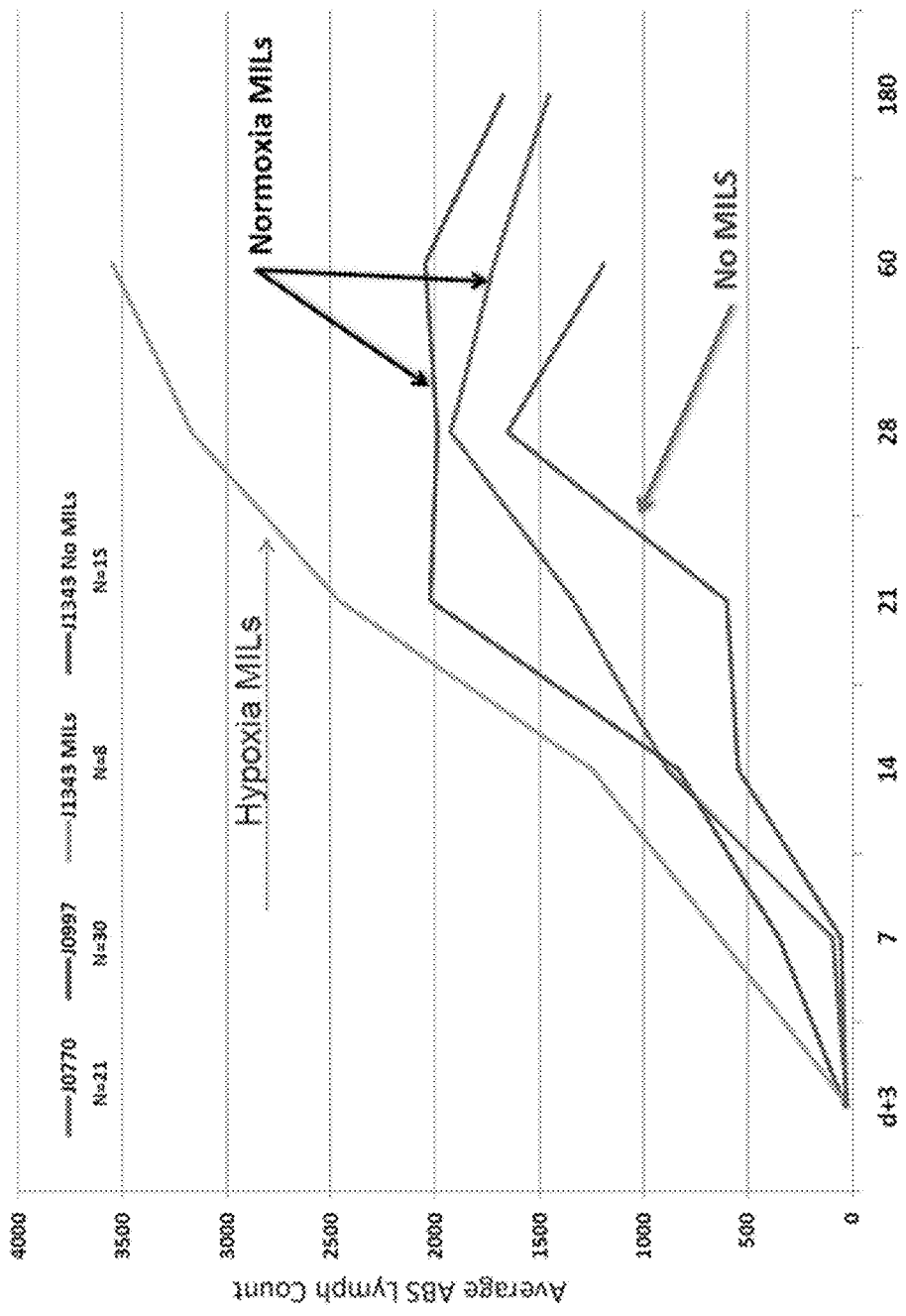
FIG. 6 is a graph that depicts the in vivo expansion of lymphocytes post-autologous transplant including in subjects receiving MILs grown under various conditions. The x-axis corresponds to the number of days post-transplant and the y-axis corresponds to the average absolute lymphocyte count per microliter for the subjects. The graph suggests that MILs grown under hypoxic conditions continue to expand in human subjects more than MILs grown under only normoxic conditions.
Figure 7:
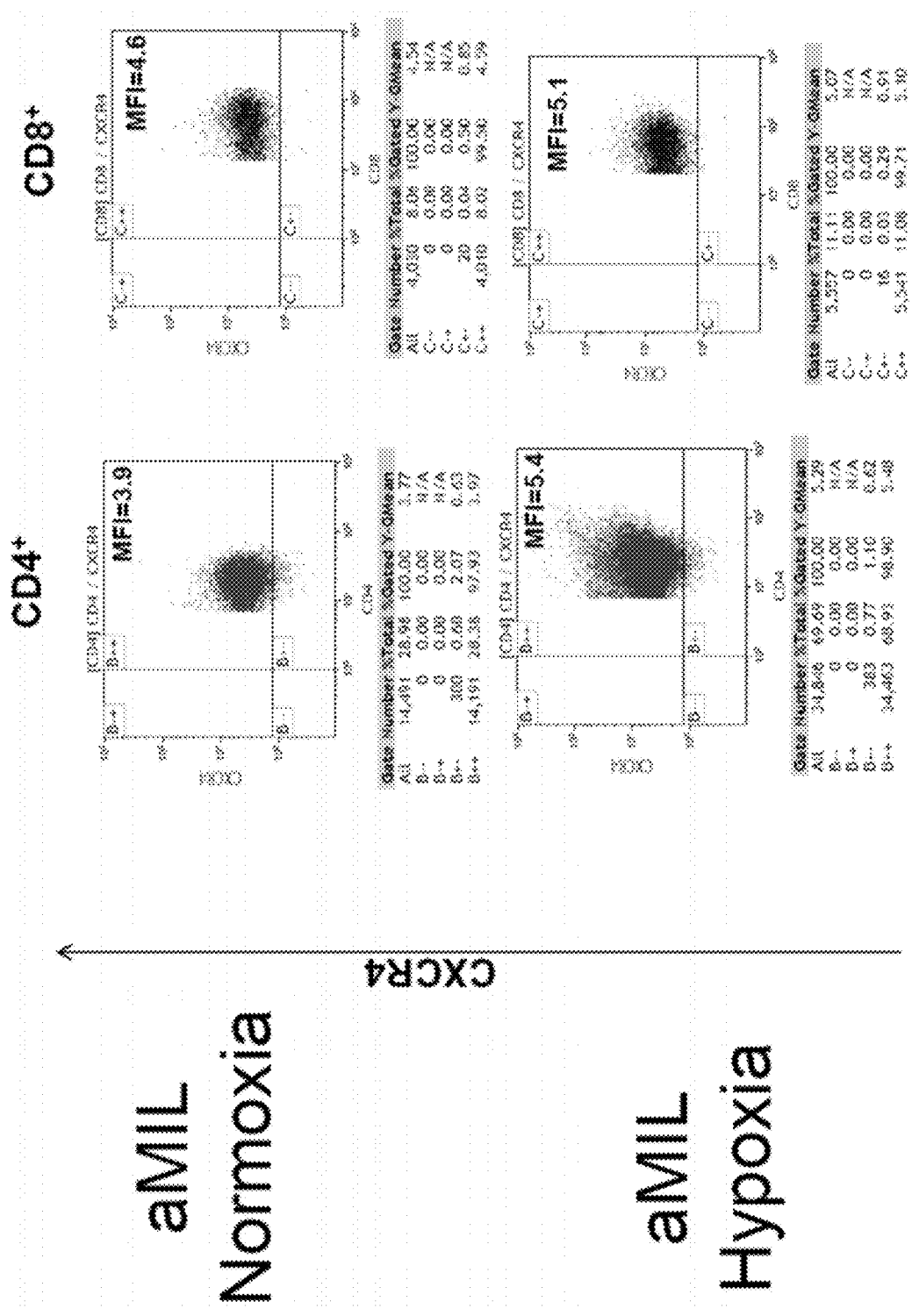
FIG. 7 depicts flow cytometry results for MILs expanded under various oxygen conditions utilizing gates for CXCR4 and either CD4 or CD8. 28.38% of the total MILs population expanded under normoxic conditions were both CXCR4 positive and CD4 positive, with a mean fluorescence intensity of 3.9. 68.91% of MILs expanded under hypoxic conditions were both CXCR4 positive and CD4 positive, with a mean fluorescence intensity of 5.4. 8.02% of MILs expanded under normoxic conditions were both CXCR4 positive and CD8 positive, with a mean fluorescence intensity of 4.6. 11.08% of MILs expanded under hypoxic conditions were both CXCR4 positive and CD8 positive. These results suggest that hypoxia increases both the number of cells expressing CXCR4 as well as degree of expression per cell (MFI), which increases the likelihood of these cells to migrate to the bone marrow upon infusion.
Figure 11:
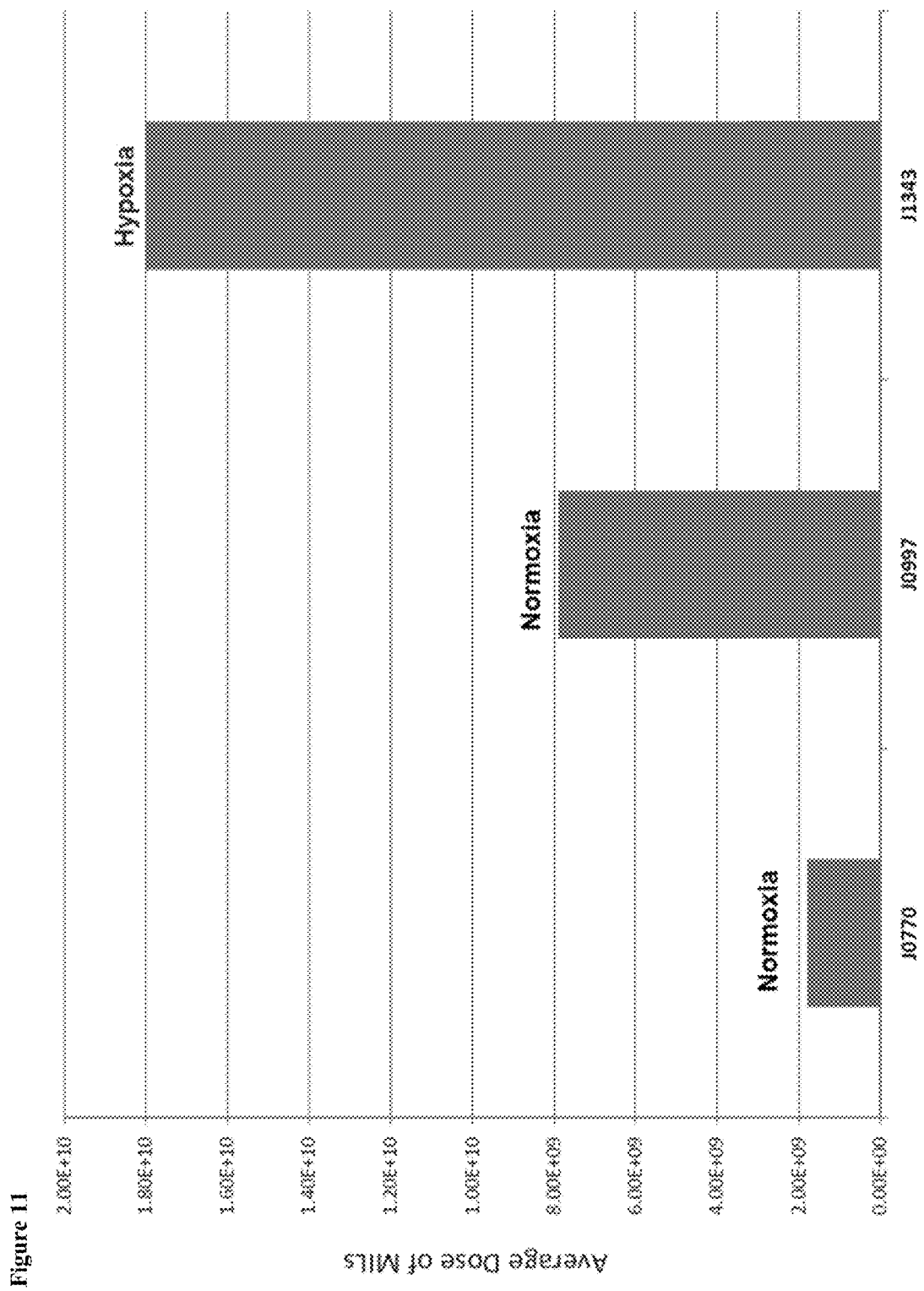
FIG. 11 is a graph that shows the ex vivo expansion of MILs. MILs expanded under hypoxic conditions resulted in a larger dose relative to MILs expanded under only normoxic conditions.

FIG. 11 shows the results of dosing for clinical treatment. In J0770, MILs were grown in static cultures in normoxic conditions. J0997—MILs were grown in the WAVE in normoxic conditions. J1343—MILs were grown for 3 days in hypoxic conditions followed by normoxic conditions. In FIG. 6 the absolute lymphocyte counts are graphed for the 3 trials post-autologous stem cell transplant. J1343 is a randomized trial in which patients either received hypoxic MILs or had no MILs infused post-transplant.

As shown in FIG. 11, the growth conditions of the present method have increased total T cell expansion from an average of 7.9E9 to 1.8E10. Furthermore, it shows for the first time in vivo T cell expansion as shown in FIG. 6, which is directly related to the efficacy of the method in treatment of patients. Depicted in the graph are the total lymphocyte counts through day 60 for a first set of patients.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. A method for treating a subject having cancer with therapeutic activated marrow infiltrating lymphocytes, the method comprising the steps of:
    (a) culturing a bone marrow sample obtained from the subject having cancer with an anti-CD3 antibody and an anti-CD28 antibody in a hypoxic environment of about 1% to about 3% oxygen to produce hypoxic-activated marrow infiltrating lymphocytes;
    (b) culturing the hypoxic-activated marrow infiltrating lymphocytes in a normoxic environment in the presence of IL-2 to produce the therapeutic activated marrow infiltrating lymphocytes; and
    (c) administering the therapeutic activated marrow infiltrating lymphocytes to the subject having cancer.

2. The method of claim 1, wherein the bone marrow sample is cultured in the hypoxic environment for about 24 hours.

3. The method of claim 1, wherein the bone marrow sample is cultured in the hypoxic environment for about 2 days.

4. The method of claim 1, wherein the bone marrow sample is cultured in the hypoxic environment for about 3 days.

5. The method of claim 1, wherein the bone marrow sample is cultured in the hypoxic environment for about 2 to about 5 days.

6. The method of claim 1, wherein the hypoxic environment is about 1% to about 2% oxygen.

7. The method of claim 1, wherein the hypoxic-activated marrow infiltrating lymphocytes are cultured in the normoxic environment for about 2 to about 12 days.

8. The method of claim 1, wherein the hypoxic-activated marrow infiltrating lymphocytes are cultured in the normoxic environment for about 6 days.

9. The method of claim 1, wherein the hypoxic-activated marrow infiltrating lymphocytes are cultured in the normoxic environment for about 9 days.

10. The method of claim 1, further comprising the step of removing a bone marrow sample from a subject having cancer prior to step (a).

11. The method of claim 1, wherein the anti-CD3 antibody and the anti-CD28 antibody are bound on a bead.

12. The method of claim 1, wherein the cancer is a hematological cancer.

13. The method of claim 1, wherein the cancer is a solid tumor.

14. The method of claim 1, wherein the cancer is lung cancer or breast cancer.

15. A method for treating a subject having cancer with therapeutic activated marrow infiltrating lymphocytes, the method comprising the steps of:
(a) culturing a bone marrow sample obtained from the subject having multiple myeloma with anti-CD3/anti-CD28 beads in a hypoxic environment of about 1% to about 2% oxygen for about 2 to about 5 days to produce hypoxic-activated marrow infiltrating lymphocytes;
(b) culturing the hypoxic-activated marrow infiltrating lymphocytes in a normoxic environment of about 21% oxygen for about 2 to about 12 days in the presence of IL-2 to produce the therapeutic activated marrow infiltrating lymphocytes; and
(c) administering the therapeutic activated marrow infiltrating lymphocytes to the subject having cancer.

16. The method of claim 15, wherein the bone marrow is cultured for about 3 days in the hypoxic environment.

17. The method of claim 15, wherein the hypoxic-activated marrow infiltrating lymphocytes are cultured for about 6 days in the normoxic environment.

18. The method of claim 15, wherein the hypoxic-activated marrow infiltrating lymphocytes are cultured for about 9 days in the normoxic environment.

19. The method of claim 15, wherein the cancer is a hematological cancer.

20. The method of claim 15, wherein the cancer is lung cancer or breast cancer.

* * * * *